United States Patent [19]

Calvet et al.

[11] Patent Number: 4,500,214
[45] Date of Patent: Feb. 19, 1985

[54] APPARATUS FOR THE CONTINUOUS MEASUREMENT OF THE HEATING POWER OF A GAS

[75] Inventors: Pierre Calvet; Bernard Platet, both of Toulouse, France

[73] Assignee: Office National d'Etudes et de Recherche Aerospatiales, Llon sous Bagneau, France

[21] Appl. No.: 424,238

[22] Filed: Sep. 27, 1982

[30] Foreign Application Priority Data

Oct. 5, 1981 [FR] France ................ 81 18722

[51] Int. Cl.³ ........................................... G01N 25/22
[52] U.S. Cl. ........................................ 374/36; 374/37; 374/38
[58] Field of Search ........................... 374/36, 37, 38

[56] References Cited

U.S. PATENT DOCUMENTS

| | | | |
|---|---|---|---|
| 2,068,791 | 1/1937 | Boys | 374/36 |
| 2,349,517 | 5/1944 | Pinkerton | 374/36 |
| 3,213,684 | 10/1965 | Seaton et al. | 374/36 |
| 3,460,385 | 9/1969 | Kolster et al. | |
| 3,472,071 | 10/1969 | Toyoda et al. | 374/36 |
| 3,665,761 | 5/1972 | Gregory | 374/31 |
| 4,036,051 | 7/1977 | Fell et al. | 374/39 |

FOREIGN PATENT DOCUMENTS

| | | |
|---|---|---|
| 238892 | 12/1910 | Fed. Rep. of Germany . |
| 255403 | 1/1913 | Fed. Rep. of Germany . |
| 466280 | 10/1913 | France . |
| 2476842 | 2/1981 | France . |

Primary Examiner—Charles Frankfort
Assistant Examiner—David R. Schuster
Attorney, Agent, or Firm—Larson and Taylor

[57] ABSTRACT

An apparatus for continuously measuring the heating power of a fuel gas comprises a calorimeter containing a vertical cell whose lower part accomodates a burner. The burner and the cell are respectively fed with fuel gas and with combustion air at a predetermined pressure and feed rate. The calorimeter has an external wall defining an annular vertical space with a wall of the cell. A dividing wall parallel to the external wall divides the annular space into concentric enclosures having a thickness which is small as compared with their length and circumferential size. The enclosures contain a same measurement gas and are operatively associated in a differential gas thermometer arrangement.

10 Claims, 2 Drawing Figures

APPARATUS FOR THE CONTINUOUS MEASUREMENT OF THE HEATING POWER OF A GAS

BACKGROUND AND SUMMARY OF THE INVENTION

The present invention relates to an apparatus for the continuous measurement of the heating power of a fuel gas, allowing the slow variations of this power to be continuously monitored.

Numerous apparatuses are already known for continuously measuring the heating power or the combustion heat of fuel gases, such as gases from natural deposits. Such installations are more especially used in cooperation with a system for measuring the flowrate in gas lines for determining the heat energy supplied to customers.

Most prior art measuring installations use thermometric detectors formed by transducers delivering an electric signal. The use of these transducers results in serious defects. The need for insulation introduces thermal resistances, the ageing of which adversely affects performances and reliability. The small area of the active surfaces of the individual transducers makes it difficult to attain a distribution over the path of the heat flux supplying a satisfactory averaging and integration of the flux densities over the whole transfer surface. The latter defect is particularly serious when the flux to be measured passes over a large-size exchange surface and presents a heterogeneous and random density distribution.

It is an object of the invention to provide an improved continuous measurement apparatus; it is a more specific object to provide an apparatus which allows satisfactory integration of the flux over the whole transfer surface area and achieves satisfactory accuracy with relatively simple means.

To this end, there is provided an apparatus for the continuous measurement of the heating power of a fuel gas, comprising a calorimeter in which is disposed an open cell whose bottom part surrounds a burner and means for supplying the burner and the cell respectively with fuel gas and combustion air at a given pressure and feedrate, characterized in that the calorimeter comprises an external wall maintained at constant temperature and defining, with the wall of the cell, an annular space divided, by means of a dividing wall parallel to the walls, into an internal enclosure and an external enclosure of small thickness with respect to their other embodiments, said enclosures being occupied by the same gas and associated together so as to form a differential gas thermometer.

It can be seen that with this arrangement any thermal contact resistance is avoided since the gas in contact with the wall of each enclosure has the same temperature as the wall of the cell, on the one hand, and the external wall, on the other. Since the thickness of the enclosures, so of the gas ducts which they contain, is small, the temperature gradient in these enclosures will be substantially normal, that is to say radial if the enclosures, and so the walls, are of revolution about an axis. The calorific inertias brought into play are small, so that the installation is capable of following the variations of heat flux produced by a flame of natural gas whose flowrate is constant whereas its composition is slowly variable.

The installation may be readily provided with calibration means. These latter may comprise a heating resistance whose effect is substituted for that of the burner. It is however preferable to use means for alternately supplying the burner with a fuel gas whose characteristics are to be measured and with a reference gas, for example pure methane when the installation is intended for measuring the heating power of natural gas.

To prevent the airflow sucked in from being appreciably affected by heating power variations of the fuel gas, it is sufficient in practice to construct the cell in the form of a duct topped by a discharge chimney having an electric heating resistance releasing a power much greater than the flux to be measured; said duct being provided with baffles for braking the air stream drawn in by convection. Thus, the heat flux variations have no real influence and there is created in the discharge chimney a natural convection current practically independent of the flux to be measured.

The gas thermometer formed from internal and external enclosures may be provided in the form of a pneumatic measuring bridge supplied by a gas source at a variable pressure following an alternate periodic law. In particular, a pneumatic measuring bridge may be used of the kind described and claimed in French Patent Publication No. 2,514,128.

The invention will be better understood from the following description of a particular embodiment, given by way of examples only.

SHORT DESCRIPTION OF THE DRAWINGS

DETAILED DESCRIPTION OF A PARTICULAR EMBODIMENT

Figure 1:
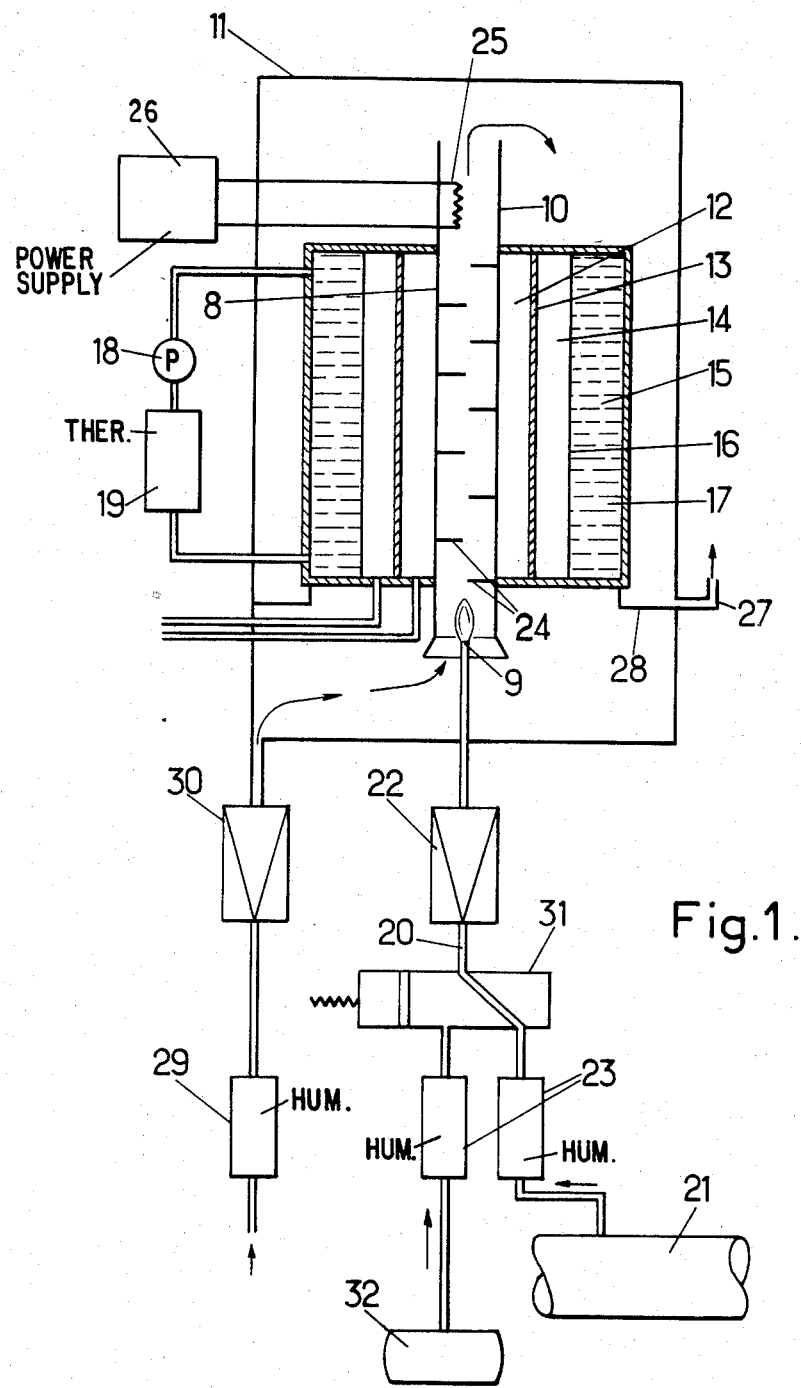
FIG. 1 is a diagram showing the main components of the calorimeter of the installation, the structural elements being shown in section through a vertical plane.

The calorimeter shown in FIG. 1 comprises a cell 8, formed by a tube which, during operation, is in a vertical position. The bottom part of the cell surrounds the nosepiece of a burner 9 which receives the gas whose heating power is to be measured. The top part of cell 8 is extended by a discharge chimney 10 whose role will appear further on and which opens into a chamber 11 whose dimensions are considerably greater than those of the chimney, through which is effected the intake of the fresh air and the discharge of burnt gases free from air currents.

Cell 8, whose length is considerably greater than its diameter, is surrounded by two concentric enclosures 12, 14, whose thickness is small with respect to their other dimensions, separated by a dividing wall 13. The wall of cell 8 separates the combustion gases coming from burner 9 from enclosure 12. Enclosure 14 is defined by an external wall 16 maintained at a uniform and constant temperature for example by means of a liquid 15 occupying an annular volume 17 belonging to a flow circuit comprising a pump 18 and a thermostat 19. Enclosures 12 and 14 have constant thickness. They will generally be cylindrical in shape, as well as the walls and the dividing wall. The opposing faces of cell 8 and wall 16 are advantageously absorbent or on the contrary reflecting to infrared radiation so as to avoid the consequences of ageing on the reflective properties of the intermediate bodies. Dividing wall 13 must be of average conductivity so that the assembly 12, 13, 14 forms a flux calorimeter in which the principal heat gradient occurs in the air layers.

The assembly formed by enclosures 12 and 14, dividing wall 13 and the walls limiting the enclosures form a thermal wall in which the heat transmission may be defined mathematically. Calculation shows that, when the enclosures have a small thickness with respect to their longitudinal and circumferential dimensions and when the temperatures vary sufficiently little in the air layers occupying enclosures 12 and 14, the mass difference between the two air layers is proportional to the total heat flux which passes through the wall, whatever the distribution of the flux density over the walls. Measurement of the mass difference is then representative of the surface integral of the flux densities, so of the total flux. Measurement of the mass difference may be effected by means of any arrangement equivalent to a gas thermometer whose enclosures form the bulbs. It is however advantageous to associate with the enclosures the pneumatic measurement bridge which will be described further on.

The burner 9 of the installation must be supplied with gas at a constant or regulated flowrate. For that, a pressure regulator 22, formed for example by a precision pressure reducing valve, is placed in the pipe 20 bringing gas to the burner 8 from duct 21 from which the sample is taken. There is further inserted in the path of the gas a conventional type humidifier 23 for saturating the gas with water vapor.

The burner operates at atmospheric pressure and precautions may be taken so that the natural convection current which occurs in cell 8 and carries with it a considerable excess of air is not affected by the variations of the heating power of the gas. This result may be attained by disposing a very stable rotary extractor above cell 8, which is provided with baffles 24 for imposing pressure losses braking the current due to the convection. It is however preferable to provide a discharge chimney 10 extending cell 8 and having at its base an electric heating resistance 25 in which an electric power supply circuit 26 dissipates a power much greater than the heat flux to be measured, due to the combustion of the gas. Thus there is created in discharge chimney 10 a natural convection current whose flowrate is practically independent of the heat flux to be measured. Chimney 10 opens into the top part of chamber 11, which is provided with a duct 27 for discharging the burnt gases. The bottom part of the chamber, separated from the top part by a transverse dividing wall 28, receives the combustion air through a humidifier 29 and a reducer 30. The conditions of use must be such that there is no condensation in the chimney: thus, the lower heating power is measured.

When the installation is used for measuring the heating power of a natural gas, it is desirable to have calibration means available. In the embodiment shown in FIG. 1, these means comprise an electromagnetic valve 31 for supplying the pressure regulator 22 and burner 9 alternately with the fuel gas to be studied and a reference gas, which will for example be pure methane contained in a pressurized bottle 32. The duration of each calibration will obviously be determined by the time required for reaching a new thermal balance: it will as a general rule be less than an hour.

Instead of an alternate supply for burner 9, an electric heating resistance may be used allowing calibration by Joule effect. But this procedure implies that the space taken up and the shape of the resistance are comparable to those of the burner, so as to create an equivalent natural convection current. It is furthermore necessary to introduce a correction factor taking into account the different radiation of the resistance and of the burner, even when the burner is surrounded by a screen whose temperature is close to that of the calibration resistance.

As was mentioned above, enclosures 12 and 14 must be associated together in a measuring unit which may be compared to a gas thermometer. In the particular case shown in FIG. 2, enclosures 12 and 14 are associated with a pneumatic bridge of the type described in the French Patent Publication No. 2,514,128 and already mentioned. The pneumatic measuring bridge comprises a gas supply, which may be air, at an alternating periodic rate. In the embodiment shown in FIG. 2, this flowrate is created by pulsed thermal expansion. The pulsing means comprise a reservoir 33 which communicates with the bridge and in which is placed a heating resistance 34 associated with an electric power supply 35 supplying square current waves. A fan 36, in permanent operation, placed in reservoir 33 adjacent the outlet thereof, maintains a permanent airflow over resistance 34 so as to cause alternating periodic pressure variations which are in practice approximately sinusoidal.

The pneumatic bridge properly speaking comprises two pressure loss elements 37 and 38 in which an alternating flow is created by reservoir 33 and which are placed respectively in series with enclosures 12 and 14. The pressure loss elements are formed by blocks pierced with passageways of a sufficiently small diameter for the flow therethrough to be laminar and so that the pressure loss is a substantially linear function of the average speed of the flow. By way of example, it may be mentioned that, in a pneumatic bridge whose alternating flow creation means operate at a frequency of the order of 1 Hz, pressure loss elements have been formed by ceramic bars 1 cm in length, pierced with a few holes of a diameter of 0.2 mm. So that the pressure losses undergone by the gas passing through elements 37 and 38 are well defined and constant, the temperature of these elements and of the gas which passes through them must also be constant. To this end, elements 37 and 38 are placed in an enclosure 39 occupied by a liquid whose temperature is constant. Enclosure 39 may further be incorporated in enclosure 17 (FIG. 1) and use the same pump 18 and the same thermostat 19.

With such an arrangement, an average overpressure may be obtained for example of the order of a third of the atmospheric pressure, with a modulation whose amplitude is a few tens of millibars.

The pressure loss elements 37 and 38 are advantageously as identical as possible with each other. Similarly, it will be generally preferable to give to enclosures 12 and 14 the same volume. Thus, pipes 40 and 41 which connect the pressure loss elements to the enclosures are at the same pressure when no imbalance occurs between the branches of the bridge.

If on the contrary an imbalance occurs, because of the difference between the average temperatures of the gases contained in enclosures 12 and 14, because of the heat flux of the flame of the burner which increases the temperature of the gas in enclosure 12 more than in enclosure 14, an alternating flow tends to circulate between enclosures 12 and 14 in a pipe 42 which connects them. Calculation shows that, as long as the temperature difference between enclosures 12 and 14 is small with respect to the average temperature of these enclosures, the pressure difference between the ends of the connecting duct is proportional to the temperature difference between the enclosures. Calculation also shows that the response of the bridge is all the better the closer the excitation frequency, fixed by the square wave generator 35, is to an optimal value which may be determined by calculation, depending on the dimensional characteristics of the bridge.

Figure 2:
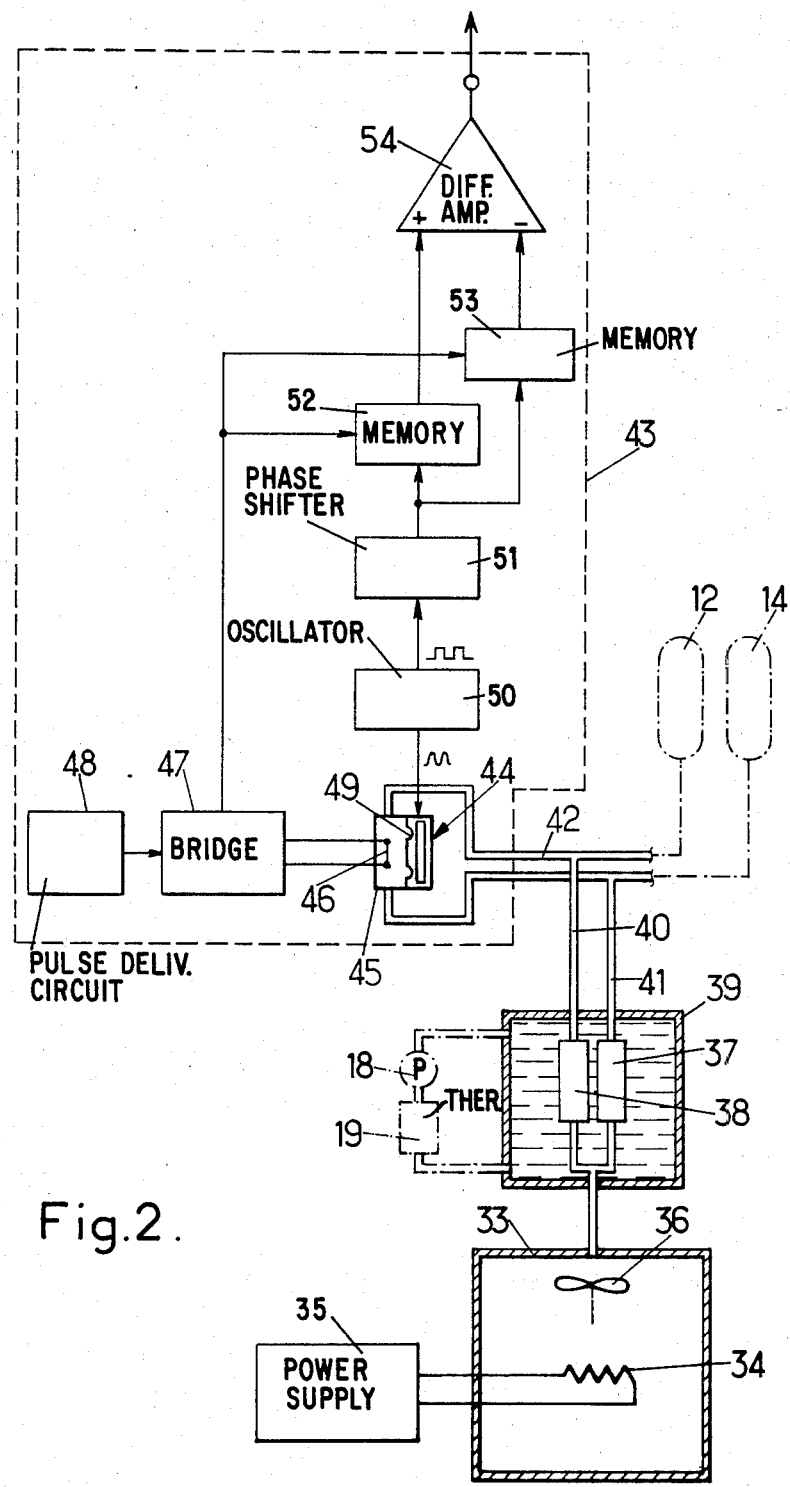
FIG. 2 is a diagram showing the construction of a pneumatic measuring bridge associated with the enclosures of the calorimeter of FIG. 1 to form a gas thermometer.

In the embodiment shown in FIG. 2, the differential pressure is measured by means of a micro flowmeter 43 of the type described and claimed in French Pat. No. 2 308 090, to which reference may be made. The construction and operation of this micro flow meter will then only be briefly described. It comprises a sensor 44 in which there is provided a chamber 45 inserted in the duct 42. In this chamber there is placed a heat resisting element 46 of small thickness placed in an electric measuring bridge 47. The bridge is supplied with power by an electric pulse heating circuit 48. On the flow between enclosures 12 and 14 which sweeps the heat-resisting element 46, there is superimposed an alternating flow at a frequency which is at least of two orders of size greater than the frequency of the pressure pulses supplied by reservoir 33. These pressure oscillations are formed by a membrane 49 energized by a coil. This latter receives a sinusoidal signal from an oscillator 50 which supplies square waves at the same frequency and with the same phase to a measuring circuit comprising a phase-shifter 51. The outputs of this phase-shifter drive the control inputs of two memories 52 and 53 which receive the measurement signals from the bridge. The signals stored in memories 52 and 53 are applied to two inputs of a differential amplifier 54 whose output delivers a measurement signal.

Thus, a measuring installation may be formed with a short response time (typically of the order of 10 mn), with low fuel consumption and allowing high accuracy to be obtained.

The invention is susceptible of numerous embodiments. For example, the burner may be supplied not at a constant rate but at a regulated rate so that the heat flux of the flame is constant. The heating power is then inferred from the flowrate. The measurement of the heat flux passing through the calorimeter may be effected by other means than those given by way of examples above.

It will of course be readily understood that the scope of the present patent is not limited to the embodiments which have been more particularly described and shown and extends to any variation remaining within the compass of equivalences.

We claim:
1. An apparatus for the continuous measurement of the heating power of a fuel gas, comprising:
   a calorimeter;
   an open cell in said calorimeter having a lower part and an upper part;
   a burner located in and surrounded by said lower part and means for supplying the burner and the cell respectively with fuel gas and combustion air at a predetermined pressure and feedrate, said calorimeter having an external wall defining an annular space with a wall of said cell;
   means for maintaining said external wall at a constant temperature;
   a dividing wall parallel to said external wall and partitioning said space into a closed internal enclosure and a closed external enclosure having thicknesses which are small as compared with their other dimensions, said internal and external enclosures being filled with respective quantities of a common measurement gas and constituting a heat transmission path from said cell to said external wall; and
   a differential gas thermometer arrangement for measuring the difference between the temperature of said common gas in said external enclosure and in said internal enclosure to thereby determine the heating power of said fuel gas.

2. Apparatus according to claim 1, wherein said cell comprises a vertical duct provided with baffles and topped by a discharge chimney and an electric heating resistor in said chimney adapted to deliver a thermal power much greater than the thermal flux due to combustion of said fuel gas in said cell.

3. Apparatus according to claim 1, further having calibration means comprising means for alternately supplying the burner with said fuel gas whose characteristics are to be measured and with a reference gas.

4. Apparatus according to claim 1, further comprising means for delivering a flow of said fuel gas to said burner at a rate of flow which is constant or controlled for maintaining the thermal flux across said enclosures at a constant value.

5. Apparatus according to claim 1, wherein said calorimeter has a single airflow path from the means for supplying the burner with combustion air up to outlet means for exiting said air and the combustion gases from combustion of said fuel gas.

6. Apparatus according to claim 1, wherein said differential gas thermometer arrangement includes a circuit for measuring the pressure difference between said enclosures, said circuit having a microflowmeter connecting said enclosures.

7. Apparatus according to claim 6, wherein each of said enclosures is connected through calibrated pressure loss means to a source of said measurement gas under a pulsating pressure whereby said two enclosures are supplied with parallel flows of said measurement gas through said calibrated pressure loss means and receive an alternating periodical rate of flow, said calibrated pressure loss means being sized to impress a head loss to the gas flows through them which is substantially in direct proportion to the rate of flow.

8. Apparatus according to claim 7, wherein the calibrated pressure loss means consist of rods formed with a plurality of passages of low diameter and maintained at a constant temperature.

9. Apparatus according to claim 8, wherein said source of measurements gas consists of a tank containing a heating electrical resistor connected to an AC power source.

10. An apparatus for the continuous measurement of the heating power of a fuel gas, comprising:
   an open cell having a lower part and an upper part;
   a burner located in and surrounded by said lower part;
   means for supplying the burner and the cell respectively with fuel gas and combustion air at a predetermined pressure and feedrate;
   an external wall defining an annular space with a cylindrical outer wall of said cell;
   means for maintaining said external wall at a constant temperature;

a dividing wall parallel to said external wall and cylindrical wall and partitioning said space into a closed internal enclosure and a closed external enclosure having thicknesses which are small as compared with their other dimensions;

a measurement gas in said internal enclosure and in said external enclosure whereby combustion of said fuel gas by said burner causes a pressure differential related to said heating power to appear between said enclosures;

a source of said measurement gas under a pressure which is variable at a predetermined frequency and which is connected to said internal and external enclosures through respective calibrated pressure loss elements, each of said pressure loss elements being so dimensioned as to subject gas flow across it to a head loss which is substantially proportional to the rate of flow of said measurement gas through it;

duct means connecting said enclosures for circulating a gas flow which is directly related to said pressure differential between said enclosures; and flow measuring means associated with said duct means, arranged for delivering an electric signal representative of the gas flow through said duct means and consequently of said heating power of said fuel gas.

* * * * *